United States Patent [19]

Haddad

[11] Patent Number: 4,535,488
[45] Date of Patent: Aug. 20, 1985

[54] ANTERIOR-POSTERIOR CHAMBER INTRAOCULAR LENS

[76] Inventor: Heskel M. Haddad, 1200 Fifth Ave., New York, N.Y. 10029

[21] Appl. No.: 431,490

[22] Filed: Sep. 30, 1982

[51] Int. Cl.³ .......................... A61F 1/16; A61F 1/24
[52] U.S. Cl. ...................................................... 623/6
[58] Field of Search ........................................ 3/13, 1

[56] References Cited

U.S. PATENT DOCUMENTS

| | | | |
|---|---|---|---|
| 2,834,023 | 5/1958 | Lieb | 3/13 X |
| 4,074,368 | 2/1978 | Levy, Jr. et al. | 3/13 |
| 4,110,848 | 9/1978 | Jensen | 3/13 |
| 4,206,518 | 6/1980 | Jardon et al. | 3/13 |
| 4,257,130 | 3/1981 | Bayers | 3/13 |
| 4,377,873 | 3/1983 | Reichert, Jr. | 3/13 |
| 4,470,159 | 9/1984 | Peyman | 3/13 |

Primary Examiner—Ronald L. Frinks
Attorney, Agent, or Firm—Blum, Kaplan, Friedman, Silberman & Beran

[57] ABSTRACT

An intraocular lens implant device comprises a small diameter lens having lateral legs extending radially therefrom. The small diameter lens extends through the iris opening to be positioned substantially in the posterior chamber of the eye while the lateral legs extend in the anterior chamber of the eye. The lateral legs provide a substantially planar surface for resting on the iris. The legs include circumferentially extended feet at the far extremities thereof. The implant is of one-piece construction. The lens is preferably of about 3 mm. in diameter.

6 Claims, 8 Drawing Figures

FIG.5
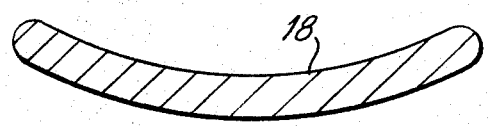
FIG.6
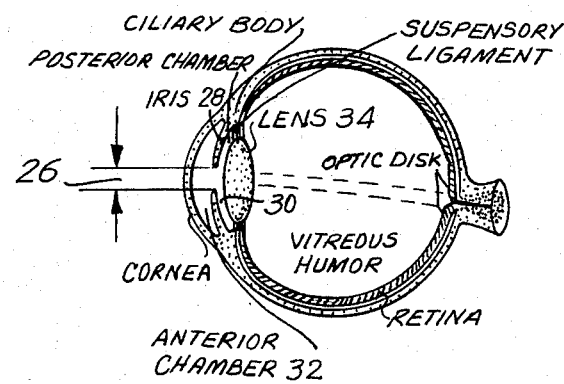
FIG.7
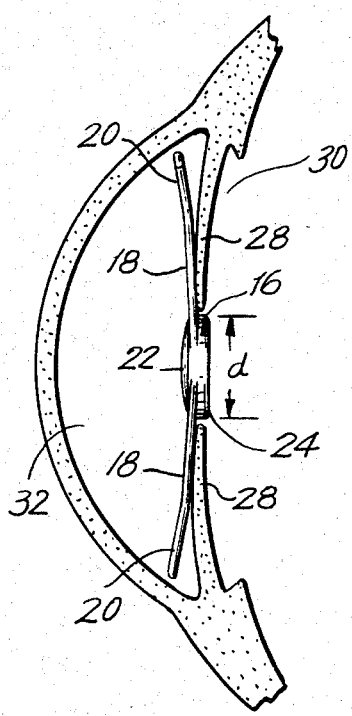
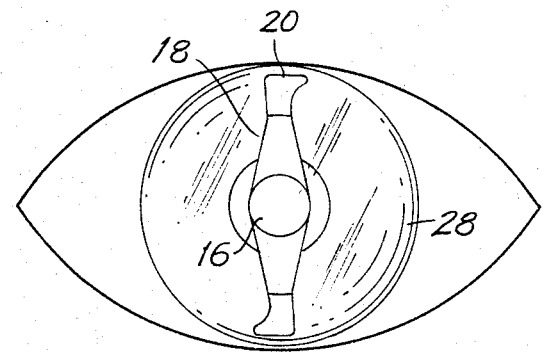
FIG.8

ANTERIOR-POSTERIOR CHAMBER INTRAOCULAR LENS

BACKGROUND OF THE INVENTION

This invention relates generally to an intracular lens implant device and more particularly to an intraocular lens implant which positions the lens substantially in the posterior chamber of the eye. Eye surgery has made remarkable progress in recent years including such accomplishments as replacement of a damaged cornea with a normal healthy cornea obtained from a recently deceased person. Additionally, a damaged or defective natural lens of the eye is being replaced by glass or plastic substitutes which are implanted within the eyeball. Such implantations are frequently performed in conjunction with cataract operations and occasionally following cataract surgery, that is, secondary implants. In these prior art implants, a lens is positioned in the anterior chamber of the eye spanning the pupil, that is, resting on the iris to cover the pupil opening area. Such implants, while achieving a significant degree of success in restoring or improving vision of the subject have been subject to certain difficulties in that glare is produced undesirably in the subject's vision due to light striking the implant lens edgewise. Also, the implanted lens frequently moves from its desired position covering the iris opening. As a result, implants have been developed, as indicated in FIGS. 1 and 2, wherein metal tabs or wires have been added to a lens which is of sufficient diameter to rest on the iris and entirely cover the pupil opening. However, these lenses also tend to move from their desired position on the iris covering the pupil and have the further disadvantage in being a costly product to produce as a result of the need to join the metal tabs or wires to a dissimilar-material lens which may be of glass or plastic. All these devices are poorly suited for secondary implants, particularly in children.

What is needed is an intraocular lens implant which reduces glare in the user's vision, stays properly positioned within the eye, is less costly to fabricate and can be easily and safely implanted in individuals who underwent cataract surgery, particularly children, through a small corneal incision.

SUMMARY OF THE INVENTION

Generally speaking, in accordance with the invention, a small diameter intraocular lens implant device especially suitable for maintaining the proper position within an eye is provided. The lens implant comprises a small diameter lens having lateral legs extending radially therefrom. The small lens diameter permits the lens to extend through the iris opening, that is, through the pupil, to be positioned substantially in the posterior chamber of the eye while the lateral legs extend in the anterior chamber of the eye. Thus, the lateral legs provide a substantially planar surface for resting on the iris. The legs include circumferentially extending feet at the far extremities thereof.

The small diameter makes the lens safe and easy to implant secondarily. The intraocular lens implant is fabricated in one piece from either glass or plastic, providing both strength and economy in production. The connection between the legs and the lens body is preferably positioned such that the lens may extend through the pupil opening into the posterior chamber when the legs rest on the iris. Thus, the intraocular lens implant in accordance with the invention, is readily located in a position better approximating the position of the natural lens. Unwanted glare is eliminated to the extent that the lens is recessed in the pupil and presents little, if any, side surface to light entering through the cornea.

Accordingly, it is an object of this invention to provide an improved intraocular lens implant device which is readily positioned within the eye and is adapted to maintain the desired position.

Another object of this invention is to provide an improved intraocular lens implant device which is of one piece construction and economical to produce.

Still another object of this invention is to provide an improved intraocular lens implant device, which when implanted positions the artificial lens in a position approximating the position of a natural lens.

A further object of this invention is to provide a small diameter intraocular lens implant device which is safely and easily secondarily implanted, particularly in children.

Still other objects and advantages of the invention will in part be obvious and will in part be apparent from the specification.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the invention, reference is had to the following description taken in connection with the accompanying drawing, in which:

FIG. 5 is a view taken along the line 5—5 of FIG. 3;

FIG. 6 is a partial cross-sectional view, with parts omitted, of the human eye;

FIG. 7 is a partial view, to an enlarged scale, similar to FIG. 6, showing the intraocular lens implant device in accordance with the invention in position, and FIG. 8 is a front view of a portion of the human eye indicating the position of the intraocular lens implant device in accordance with the invention.

DESCRIPTION OF THE PREFERRED EMBODIMENTS

Figure 1:
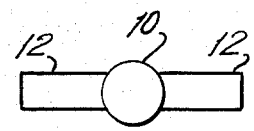
FIG. 1 is an intraocular lens implant device of the prior art.
Figure 2:
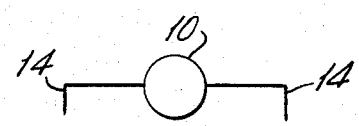
FIG. 2 is another intraocular lens implant device of the prior art.

FIGS. 1 and 2 illustrate intraocular lens implant devices of the prior art including a lens 10 fabricated of plastic or glass to which a pair of opposed lateral tabs 12 in the form of loops of wire (FIG. 1) or bent wires 14 (FIG. 2) are attached. The lenses 10 have a 6 mm. diameter spanning the pupil such that the device rests upon the iris of the eye with the lens 10 extending into the anterior chamber (FIG. 6). Tabs 12 and bent wires 14 aid in preventing motion of the lens 10 relative to the pupil opening in the iris of the eye by interacting with the iris or other tissue in the anterior chamber of the eye. However, positioning of the lens 10 is not always satisfactorily maintained and the position of the lens 10 in the anterior chamber causes glare in the sight of the user as the edge of the lens catches the incoming light.

Figure 3:
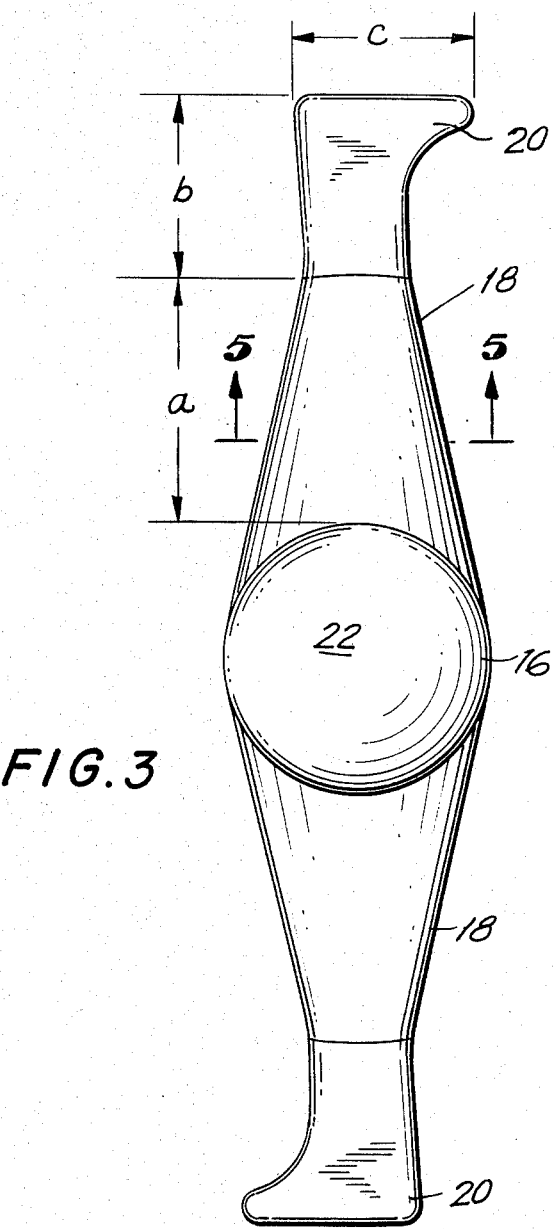
FIG. 3 is a front view to an enlarged scale of an intraocular lens implant device in accordance with the invention.
Figure 4:
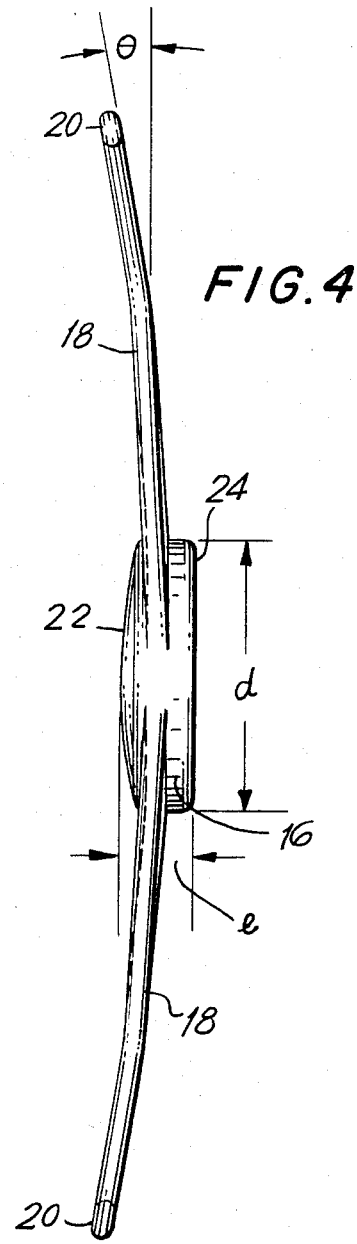
FIG. 4 is a side elevational view of the intraocular lens implant device of FIG. 3.

The intraocular lens implant device, in accordance with the invention, is designed to overcome the difficulties described above. With reference to FIG. 3, the intraocular lens implant in accordance with the invention, includes a lens 16 having a pair of legs 18 extending from the lens 16 in opposite directions. Each leg tapers linearly as it extends from the lens 16 and terminates in a circumferentially extending foot 20. Smooth lines join the legs 18 to the feet 20 and the legs 18 to the lens 16. As shown in FIGS. 4 and 5, the legs 18 and feet 20 are substantially planar and thin. The legs 18 are attached to the lens 16 close to the anterior surface 22 of the lens 16 such that the posterior surface 24 lens 16 is set away from the generally planar surface of the legs 18.

The intraocular lens implant device in accordance with the invention is an integral element, the legs 18 with feet 20 being formed with the lens 16 in the production of the device either from plastic or glass. The lens 16 is formed with optical curvatures known in the art to suit the intended purpose, and accordingly, receives no further detailed description herein. The diameter d of the lens 16 is sufficiently small such that the lens 16 passes through the pupil opening 26 in the iris 28 of the eye (FIGS. 6, 7). As best illustrated in FIG. 7, the lens 16 extends substantially into the posterior chamber 30 of the eye with the legs 18 and feet 20 being in the anterior chamber 32, resting in the angle of the anterior chamber.

As illustrated in FIG. 5, the legs 18 have a slight camber such that the legs 18 curve away from the surface of the iris 28 at the lateral extremities of the legs. Additionally, the feet 20, join the legs 18 at an angle $\theta$ (FIG. 4) and extend further away from the iris 28 and into the anterior chamber 32. This curvature of the legs 18 and deflection of the feet 20 away from the iris 28 facilitates a strong attachment between the eye tissues and the legs 18 and feet 20. Thus, the intraocular lens implant device in accordance with the invention takes a position in the eye which substantially duplicates the position of the natural lens 34 (FIG. 6) in the eye, reducing side glare thereby. Also, by the lens passing through the pupil opening 26 in the iris 28, and being substantially in the posterior chamber 30, the lens 16 remains firmly centered in the eye (FIGS. 7, 8). Because of the small portion of the lens 16 which extends into the anterior chamber 32, glare is reduced in the user's vision resulting from light striking the side surfaces of the lens 16. Thus, the objects of the invention are achieved, providing more positive centering and improved vision as compared to the prior art.

An embodiment (FIGS. 3, 4, 5) of an intraocular lens implant in accordance with the invention which performed satisfactorily included a lens having a diameter of 3 millimeters. Approximately three-quarters of the axial thickness l of the lens is in the posterior chamber 30 of the eye. The length a of the leg 18 is 3 millimeters and the length b from the connection between the leg 18 and the foot 20 to the end of the foot 20 is 2 millimeters. The circumferential length c of the foot 20 is 2 millimeters. The camber (FIG. 5) in the legs 18 represents approximately 5° of arc in a circle and the angle $\theta$ (FIG. 4) is in the order of 5°.

The small size of the intraocular lens implant device in accordance with the invention permits its insertion through a small opening cut in the cornea. Such a small incision minimizes the danger of the implant procedure and greatly speeds the recovery period. The lens implant device make for easier and safer implants in children and infants after cataract surgery.

Although the legs 18 and feet 20 have been described above and illustrated in the Figures entirely in the anterior eye chamber it should be understood that in alternative embodiments of an intraocular lens implant device in accordance with the invention, the legs may be curved to enter the pupil opening prior to connection with the lens 16. Thus, the legs and feet may be anchored in the anterior chamber as described above, while the lens 16 is positioned in alignment with the pupil opening with the anterior lens surface 22 being in either the anterior or posterior chamber, or flush with the iris.

It will thus be seen that the objects set forth above, among those made apparent from the preceding description, are efficiently attained and, since certain changes may be made in the above construction without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described, and all statements of the scope of the ivention, as a matter of language might be said to fall therebetween.

What is claimed is:

1. An intraocular lens implant device for an eye having anterior and posterior chambers and an iris partially separating said chambers, said iris having a pupil opening therethrough, comprising:
    a lens dimensioned to fit within said pupil opening; and
    two support legs each attached at one end to said lens and extending laterally from said lens, said support legs being adapted to engage the tissues of said eye entirely in said anterior chamber and being adapted to hold said lens without use of sutures or pegs in a position within said eye at which said lens is aligned with said pupil opening and extends through said pupil opening in part into said posterior chamber, at least one leg being adapted to make contact with a surface of the iris in the anterior chamber, said at least one leg being cambered in transverse cross-section, said camber being adapted to reduce the area of contact between the iris surface and said at least one leg, whereby said lens implant device may be implanted through a small corneal incision.

2. An intraocular lens implant device for an eye having anterior and posterior chambers and an iris partially separating said chambers, said iris having a pupil opening therethrough, comprising:
    a lens dimensioned to fit within said pupil opening; and
    two support legs each attached at one end to said lens and extending laterally from said lens, said support legs being adapted to engage the tissues of said eye entirely in said anterior chamber and being adapted to hold said lens without use of sutures or pegs in a position within said eye at which said lens is aligned with said pupil opening and extends through said pupil opening in part into said posterior chamber, at least one leg further including a foot attached to the other end thereof, said foot extending perpendicularly to the length of said at least one leg, said at least one leg and foot intersecting at an angle, said angle being adapted to project said foot away from said iris surface and further into said anterior chamber, whereby said lens implant device may be implanted through a small corneal incision.

3. An intraocular lens implant device as claimed in claim 2, wherein said at least one leg is cambered in transverse cross-section, said camber being adapted to reduce the area of contact between said iris surface and said at least one leg.

4. An intraocular lens implant device as claimed in claim 3, wherein each of said legs has a foot and is cambered, said leg camber is circular and each of said feet and the associated leg intersect one another at an angle approximately 5°.

5. An intraocular lens implant device as claimed in claim 2, wherein each of said legs has a foot and is cambered in transverse cross-section, said leg camber is circular, and each of said feet and the associated leg intersect one another at an angle approximately 5°.

6. An intraocular lens implant device as claimed in claim 5, wherein said lens and support legs are adapted so that the extension of said lens in said posterior chamber exceeds the extension of said lens into said anterior chamber.

* * * * *